US007731954B2

United States Patent
Davis et al.

(10) Patent No.: US 7,731,954 B2
(45) Date of Patent: Jun. 8, 2010

(54) WOUND DRESSINGS COMPRISING HYDRATED HYDROGELS AND ENZYMES

(75) Inventors: Paul James Davis, Bedford (GB);
Andrew John Austin, Northants (GB)

(73) Assignee: Insense Limited, Bedford (GB)

( * ) Notice: Subject to any disclaimer, the term of this patent is extended or adjusted under 35 U.S.C. 154(b) by 86 days.

(21) Appl. No.: 10/512,440

(22) PCT Filed: Apr. 23, 2003

(86) PCT No.: PCT/GB03/01738

§ 371 (c)(1),
(2), (4) Date: Oct. 25, 2004

(87) PCT Pub. No.: WO03/090800

PCT Pub. Date: Nov. 6, 2003

(65) Prior Publication Data

US 2006/0034816 A1 Feb. 16, 2006

(30) Foreign Application Priority Data

Apr. 24, 2002 (EP) .................................. 02252895
May 18, 2002 (GB) .................................. 0211504.6

(51) Int. Cl.
*A61K 38/44* (2006.01)
(52) U.S. Cl. ...................... 424/94.4; 435/174; 435/189
(58) Field of Classification Search ................ 424/94.4, 424/94.2; 435/25, 28, 175, 176, 177, 182, 435/189, 190
See application file for complete search history.

(56) References Cited

U.S. PATENT DOCUMENTS

| | | | |
|---|---|---|---|
| 3,546,070 A | 12/1970 | Yoshinaga | |
| 4,010,259 A | 3/1977 | Johansson | |
| 4,278,548 A | 7/1981 | Bettinger et al. | |
| 4,312,833 A | 1/1982 | Clough et al. | |
| 4,327,731 A | 5/1982 | Powell | |
| 4,391,799 A | 7/1983 | Mason et al. | |
| 4,452,892 A | 6/1984 | Rosevear | ................. 435/176 |
| 4,476,108 A | 10/1984 | Kessler et al. | |
| 4,576,817 A | 3/1986 | Montgomery et al. | ......... 424/94 |
| 4,657,864 A * | 4/1987 | Lo | ............................ 435/192 |
| 4,746,514 A | 5/1988 | Warne | ........................ 424/445 |
| 4,775,626 A | 10/1988 | Armenta et al. | |
| 4,783,448 A | 11/1988 | Johansson | |
| 5,196,190 A | 3/1993 | Nangia et al. | |
| 5,232,914 A | 8/1993 | Fellman | |
| 5,372,802 A | 12/1994 | Barrows et al. | |
| 5,399,353 A | 3/1995 | Bartnik et al. | |
| 5,455,042 A | 10/1995 | Sakai et al. | |
| 5,483,697 A | 1/1996 | Fuchs | |
| 5,552,316 A | 9/1996 | Savage | |
| 5,607,681 A | 3/1997 | Galley et al. | |
| 5,648,075 A | 7/1997 | Kessler et al. | |
| 5,652,274 A | 7/1997 | Martin | |
| 5,696,456 A * | 12/1997 | Lee | ............................ 326/70 |
| 5,762,638 A | 6/1998 | Shikani et al. | |
| 5,792,090 A * | 8/1998 | Ladin | ........................ 602/48 |
| 5,804,213 A * | 9/1998 | Rolf | ........................... 424/445 |
| 5,849,241 A | 12/1998 | Connan | |
| 6,103,275 A | 8/2000 | Seitz et al. | |
| 2001/0041188 A1 | 11/2001 | Gibbins et al. | |
| 2002/0006634 A1 | 1/2002 | Han et al. | ..................... 435/25 |
| 2002/0037270 A1 | 3/2002 | Munro | |
| 2003/0082225 A1 | 5/2003 | Mason | |
| 2003/0225356 A1 | 12/2003 | Kulichikhin et al. | |
| 2005/0181026 A1 | 8/2005 | Davis et al. | |
| 2006/0275350 A1 | 12/2006 | Davis et al. | |
| 2006/0281165 A1 | 12/2006 | Davis et al. | |
| 2007/0148117 A1 | 6/2007 | Davis et al. | |

(Continued)

FOREIGN PATENT DOCUMENTS

DE 40 26 153 2/1992

(Continued)

OTHER PUBLICATIONS

Carlsson "Bactericidal effect of hydrogen peroxide is prevented by the lactoperoxidase-thiocyanate system under anaerobic conditions" Infection and Immunity 1190-1192 (1980).

(Continued)

*Primary Examiner*—Leon B. Lankford
*Assistant Examiner*—Susan E. Fernandez
(74) *Attorney, Agent, or Firm*—Morgan Lewis & Bockius LLP (57) ABSTRACT

A skin dressing, particularly a wound dressing, comprises oxidoreductase enzyme and, optionally, peroxidase enzyme, wherein the enzyme(s) are present in hydrated condition, e.g. being present in one or more hydrated hydrogels. The dressing is used by being located on the skin of a human or animal e.g. over a wound. The oxidoreductase enzyme catalyses a reaction that produces hydrogen peroxide from an appropriate substrate, the substrate either being naturally present in body fluids and/or being supplied separately and/or being incorporated into the dressing. The currently preferred oxidoreductase enzyme is glucose oxidase. The catalyses reaction of β-D-glucose substrate to give hydrogen peroxide and gluconic acid. A mixture of oxidoreductase enzyme can undergo reaction (optionally catalysed by the peroxidase enzyme) to produce a variety of species including reactive oxygen intermediates that have antimicrobial properties and that can therefore assist in promoting wound healing.

17 Claims, 3 Drawing Sheets

U.S. PATENT DOCUMENTS

| | | |
|---|---|---|
| 2007/0190122 A1 | 8/2007 | Davis et al. |
| 2009/0081279 A1 | 3/2009 | Jezek et al. |
| 2009/0169600 A1 | 7/2009 | Davis et al. |

FOREIGN PATENT DOCUMENTS

| | | |
|---|---|---|
| EP | 0307376 | 3/1989 |
| EP | 1429617 | 6/2004 |
| GB | 2 024 012 B | 1/1980 |
| WO | WO 91/11105 | 8/1991 |
| WO | WO 94/04127 | 3/1994 |
| WO | WO 97/02811 | 1/1997 |
| WO | WO 98/20015 | 5/1998 |
| WO | WO 98/22513 | 5/1998 |
| WO | WO 9912581 A2 * | 3/1999 |
| WO | WO 99/65538 | 12/1999 |
| WO | WO 01/28600 A1 | 4/2001 |
| WO | WO 01/96422 A1 | 12/2001 |
| WO | WO 01/98286 | 12/2001 |
| WO | WO 03/017989 | 3/2003 |
| WO | WO 03/090800 | 11/2003 |
| WO | WO 2004/091675 | 10/2004 |
| WO | WO 2004/093786 | 11/2004 |
| WO | WO 2004/108176 | 12/2004 |
| WO | WO 2004/108917 | 12/2004 |
| WO | WO 2004/112851 | 12/2004 |
| WO | WO 2005/072783 | 8/2005 |
| WO | WO 2005/072784 | 8/2005 |
| WO | WO 2006/062679 | 6/2006 |
| WO | WO 2006/095193 | 9/2006 |
| WO | WO 2007/134304 | 11/2007 |
| WO | WO 2008/009925 | 1/2008 |

OTHER PUBLICATIONS

Sohail et al. "Divalent Cation Induced Changes in Structural Properties of the Dimeric Enzyme Glucose Oxidase: Dual Effect of Dimer Stabilization and Dissociation with Loss of Cooperative Interactions in Enzyme Monomer" Biochemistry 41(22):7142-7149 (2002).

Graf et al., "Method for Determination of Hydrogen Peroxide, with Its Application Illustrated by Glucose Assay", Clin. Chem., 26(5):658-660 (1980).

Kompendium Pharma. '98 (handbook for the pharmaceutical preparation of non-standard pharmacy products) with translation of p. 224.

* cited by examiner

WOUND DRESSINGS COMPRISING HYDRATED HYDROGELS AND ENZYMES

FIELD OF THE INVENTION

This invention relates to skin dressings for application to a part of a human or animal body for treatment of skin, and relates particularly (but not exclusively) wound dressings for treatment of compromised skin, particularly skin lesions, i.e. any interruption in the surface of the skin, whether caused by injury or disease, including skin ulcers, burns, cuts, punctures, lacerations, blunt traumas, acne lesions, boils etc.

BACKGROUND TO THE INVENTION

Wounds frequently become infected. Wound dressings may carry antiseptic substances, and the physical protection they provide prevents ingress of extra infecting microbes, although this microbial exclusion is seldom absolute. Antiseptic substances carried on the dressing pad are not usually very effective, possibly because they do not readily diffuse into the wound at a steady rate. Moreover, the most effective substances, antibiotics, are not available for routine use, because of the ever-present problems of emerging drug resistance.

Hydrogen peroxide ($H_2O_2$) is a known antimicrobial substance with many advantages. It is produced naturally in the body by white blood cells as part of the immune defence activities in response to infection. There are no known microbial evasion mechanisms by which microbes can escape its effects and it has a short lifetime, very rapidly breaking down to water and oxygen in the tissues. It therefore does not accumulate to dangerous levels. When it is to be applied topically (e.g. to treat acne), its effectiveness is enhanced by the fact that it readily penetrates the skin surface to reach underlying sites of infection.

As hydrogen peroxide is so beneficial, it has been used for many years as an anti-microbial substance for cleansing wounds of all kinds and as a biologically compatible general antiseptic. In particular, hydrogen peroxide-containing ointments have been used, e.g., for treatment of leg ulcers, pressure sores, minor wounds and infection. There are, however, problems associated with the use of hydrogen peroxide. Hydrogen peroxide solution is very unstable and is readily oxidised to water and oxygen; further, hydrogen peroxide at high concentration can be damaging to normal skin and to cells responsible for healing in the wound bed. It is very difficult or even impossible to use hydrogen peroxide as part of a pre-dosed wound dressing: it's instability would make for a product with an impossibly short shelf-life, and dosing at the point of application would still not provide a sustained delivery over a usefully prolonged period. When it is used in wound treatment (as described in the British Pharmacopoeia, for example) very high concentrations (typically 3%) are needed to achieve a powerful antimicrobial effect over a very short time interval. Even this type of short burst can be effective, because of the great effectiveness of hydrogen peroxide, but there is the further disadvantage that such high concentrations can be relatively damaging to host cells and can impede the healing process. For this reason, use of hydrogen peroxide tends to be restricted to initial clean-up and sterilisation of wounds. Even so, it is a natural defence substance, produced by the body's own cells (at lower concentrations) and it is increasingly recognised as an intercellular and intracellular messenger molecule, involved in cell to cell molecular signalling and regulation. Undoubtedly, hydrogen peroxide is potentially a very beneficial molecule, if it can be used at the right concentrations and in the appropriate time course.

U.S. Pat. No. 4,576,817 proposes a bacteriostatic fibrous wound dressing incorporating dry enzymes such as glucose oxidase and lactoperoxidase to generate e.g. hydrogen peroxide and hypoiodite on contact with serum.

WO 01/28600 discloses a wound dressing including dry glucose oxidase, dry lactoperoxidase and an iodide salt in a polymeric matrix. The glucose oxidase catalyses an oxidation reaction of glucose present in body fluids of a wound site to generate hydrogen peroxide. The action of lactoperoxidase on hydrogen peroxide and iodide generates elemental iodine, which is a powerful anti-infective agent.

Efficient wound healing is promoted by several factors, including a moist environment and the removal of wound exudates by absorption. Dry super-absorbent materials have often been used to gain the benefit of exudate removal, since these substances readily take up and hold fluids that exude from wounds with great efficiency. However, a highly efficient dry absorbent material can lead to an unhelpful lack of moisture, and a wound dressing constructed from such a material would not work well with antimicrobial enzymic systems, at least not until the dressing had become thoroughly wetted by wound fluid.

SUMMARY OF THE INVENTION

The present invention provides a skin dressing comprising oxidoreductase enzyme and optionally peroxidase enzyme, wherein the enzyme(s) are present in hydrated condition. The enzyme(s) are in hydrated condition in the dressing prior to use of the dressing, i.e. prior to application of the dressing to skin, and so also in the dressing when sealed in packaging.

By providing the enzyme(s) in hydrated condition, the enzyme is present in a wet, active state in the dressing and can begin functioning immediately when brought into contact with appropriate substrate on use of the dressing. This is to be contrasted with prior art dressings where enzymes are in dry condition and require initial hydration on use, thus delaying enzyme functioning and consequent antimicrobial effects. The hydrated state of the enzyme also allows it to be formulated into a moist hydrogel or other moist dressing material in such a way that the dressing can donate moisture to a dry wound.

The dressing is used by being located on the skin of a human or animal e.g. over a wound or on a region of skin to be treated for cosmetic or therapeutic purposes, e.g. for treatment of acne or other skin conditions. The oxidoreductase enzyme catalyses a reaction of an appropriate substrate with oxygen to produce hydrogen peroxide. The substrate may either be naturally present in body fluids and/or be supplied separately and/or be incorporated into the dressing. Oxidoreductase enzymes suitable for use in the invention and the corresponding substrates (which are present in blood and tissue fluids) include the following:

| Enzyme | Substrate |
| --- | --- |
| Glucose oxidase | β-D glucose |
| Hexose oxidase | Hexose |
| Cholesterol oxidase | Cholesterol |
| Galactose oxidase | D-galactose |
| Pyranose oxidase | Pyranose |
| Choline oxidase | Choline |
| Pyruvate oxidase | Pyruvate |
| Glycollate oxidase | Glycollate |
| Aminoacid oxidase | Aminoacid |

The currently preferred oxidoreductase enzyme is glucose oxidase. This catalyses reaction of β-D-glucose substrate to give hydrogen peroxide and gluconic acid.

A mixture of oxidoreductase enzymes may be used.

If the reaction occurs on or in the vicinity of the skin, the hydrogen peroxide so produced can have a localised antibacterial effect.

Alternatively or additionally, the hydrogen peroxide generated in this way may be used in a two stage arrangement, with the hydrogen peroxide undergoing a reaction catalysed by a peroxidase enzyme to produce a variety of species including reactive oxygen intermediates that have antimicrobial properties and that can therefore assist in promoting wound healing. For such embodiments, the dressing includes a peroxidase enzyme, preferably present in hydrated condition. As a further possibility the hydrogen peroxide can react directly in a non-catalysed manner with substances such as iodide ions to generate molecular iodine.

Peroxidase enzymes useful in the invention include lactoperoxidase, horseradish peroxidase, iodide peroxidase, chloride peroxidase and myeloperoxidase, with lactoperoxidase currently being favoured.

A mixture of peroxidase enzymes may be used.

The active species produced by the action of peroxidase are difficult to define, and will to some extend depend the particular peroxidase in question. For example, horse radish peroxidase works very differently to lactoperoxidase. The detailed chemistry is complicated by the fact that the products are so reactive that they rapidly give rise to other, associated products that are also very reactive. It is believed that hydroxyl radicals, singlet oxygen and superoxide are produced, just as in the "oxidative burst" reactions identified in neutrophil and macrophage leukocytes of the human body, and in the well known "Fenton" reaction, based on the catalytic effects of ferric ions.

The dressing includes a source of water so that the enzyme or enzymes are present in hydrated condition. The dressing may be in the form, e.g. of a moist cotton dressing or may include a structured wick material with moist ingredients. Preferably, however, the dressing includes one or more water-based or aqueous gels, also referred to as hydrated hydrogels. Such gels may be formed of a variety of materials and may contain a variety of reagents, as will be discussed below.

A hydrated hydrogel provides a source of water for hydrating the enzyme or enzymes, promoting rapid reaction and consequent release of antimicrobial substances. The gel can also act to absorb water and other materials exuded from a wound site, enabling the dressing to perform a valuable and useful function by removing such materials from a wound site. The hydrated hydrogel also provides a source of moisture, that can function to maintain the enzyme or enzymes in the dressing in hydrated condition, and that can act in use to maintain a wound site moist, aiding healing.

The or each hydrated hydrogel conveniently comprises hydrophilic polymer material. Suitable hydrophilic polymer materials include polyacrylates and methacrylates, e.g. as supplied by First Water Ltd in the form of proprietory hydrogels, including poly 2-acrylamido-2-methylpropane sulphonic acid (polyAMPS) or salts thereof (e.g. as described in WO 01/96422), polysaccharides e.g. polysaccharide gums particularly xanthan gum (e.g. available under the Trade Mark Keltrol), various sugars, polycarboxylic acids (e.g. available under the Trade Mark Gantrez AN-169 BF from ISP Europe), poly(methyl vinyl ether co-maleic anhydride) (e.g. available under the Trade Mark Gantrez AN 139, having a molecular weight in the range 20,000 to 40,000), polyvinyl pyrrolidone (e.g. in the form of commercially available grades known as PVP K-30 and PVP K-90), polyethylene oxide (e.g. available under the Trade Mark Polyox WSR-301), polyvinyl alcohol (e.g. available under the Trade Mark Elvanol), cross-linked polyacrylic polymer (e.g. available under the Trade Mark Carbopol EZ-1), celluloses and modified celluloses including hydroxypropyl cellulose (e.g. available under the Trade Mark Klucel EEF), sodium carboxymethyl cellulose (e.g. available under the Trade Mark Cellulose Gum 7LF) and hydroxyethyl cellulose (e.g. available under the Trade Mark Natrosol 250 LR).

Mixtures of hydrophilic polymer materials may be used in a gel.

In a hydrated hydrogel of hydrophilic polymer material, the hydrophilic polymer material is desirably present at a concentration of at least 1%, preferably at least 2%, more preferably at least 5%, possibly at least 10%, by weight based on the total weight of the gel.

By using a gel comprising a relatively high concentration (at least 2% by weight) of hydrophilic polymer material, the gel can function particularly effectively to take up water in use of the dressing, e.g. from serum exudates while in contact with a wound. Because the gel is an aqueous system, use of the dressing does not have the effect of inducing an overall dryness of the wound which would be undesirable. This is because water vapour pressure is maintained in the enclosed environment surrounding the skin in use of the dressing. The gel thus functions as an absorbent entity for the removal of moisture, e.g. wound exudate, that also provides a helpful background level of moisture.

The water-uptake capacity of a hydrated hydrogel, including a high concentration gel, enables the dressing to aid wound healing by removing substantial amounts of exudates, swelling-up as it does so. By using a carefully formulated, ready-hydrated gel, the wound is prevented from reaching a state of unhelpful dryness. Ready hydration also ensures the quick formation of a liquid interface between the dressing and the wound, thus preventing adhesion, which otherwise would interfere with easy lifting of the dressing when it has to be replaced. A good liquid interface between the wound and the dressing is also important in allowing the antimicrobial products of the enzymes to enter the wound through all of the available surface.

The or each gel may contain various reagents, including one or more of the following:

one or more oxidoreductase enzymes;
one or more peroxidase enzymes;
substrate for the oxidoreductase enzyme (to be discussed below);
a source of iodide ions (to be discussed below);
glycerol (which acts as a humectant and moisturiser), typically in an amount up to 20% by weight of the weight of the gel.

In particular, the enzyme or enzymes may be present in one or more hydrated hydrogels.

For example, one of the enzymes, oxidoreductase enzyme or peroxidase enzyme, may be present in a gel, e.g. an aqueous high concentration hydrophilic polymer material gel. As a further possibility both enzymes may be present in a gel, e.g. such a high concentration gel. A further option is for each enzyme to be present in a respective gel, e.g. an aqueous high concentration hydrophilic gel.

As a further possibility, the dressing may include a single hydrated hydrogel (e.g. of poly AMPS), containing no enzymes but possibly containing substrate for the oxidoreductase enzyme (e.g. a source of glucose for glucose oxidase), additionally or alternatively containing a supply of iodide ions (e.g. in the form of one or more iodide salts) and optionally also containing glycerol.

The or each gel may be cross-linked. For example, the gel may comprise an alginate gel, e.g. formed from alginic acid cross-linked in known manner, e.g. by use of calcium chloride. Cross-linked gels form an entrapping biopolymer matrix that can retain the enzyme within the gel if the degree of cross-linking is sufficiently tight, thus preventing release of the enzyme into the wound bed in use of the dressing. The gel may be in the form of beadlets, beads, slabs or extruded threads etc.

The hydrated hydrogel, particularly a cross-linked gel, may be cast around a mechanical reinforcing structure, such as a sheet of cotton gauze or an inert flexible mesh, e.g. to providing a structurally reinforced hydrogel layer or slab.

The hydrated hydrogel may alternatively be in the form of a non-cross-linked shear-thinning gel, e.g. of suitable gums such as xanthan gum (e.g. available under the Trade Mark Keltrol), in this case preferably without a mechanical reinforcing structure. Such gums are liquid when subjected to shear stress (e.g. when being poured or squeezed through a nozzle) but set when static. Thus the gel may be in the form of a pourable component, facilitating production of gels in the dressing. Such a shear-thinning gel may also be used in combination with a preformed, mechanically reinforced gel, as discussed above.

The water-absorbing gel may utilise an increased concentration of hydrophilic substance, which may be the actual gel-forming polymer material, e.g. polysaccharide, itself or an additional substance added into the mixture for the sole purpose of absorbing water. One example of this type of functional mixture is that formed by a combination of cross-linked alginate at about 2% by weight and xanthan gum at about 5-10% by weight, based on the total weight of the gel. A particularly favoured version is that of covalently linked polymeric hydrogel such as polyAMPS, which is strongly water absorbing, being able to take up very large volumes of water or aqueous solutions.

The enzyme or enzymes may be present in a gel in a number of possible forms, including in solution as free molecules. To improve efficiency of retention of the enzymes in the gel, the enzymes may be chemically conjugated to each other, chemically conjugated to other molecules (e.g. polyethylene imine), or incorporated in a solid support such as beads.

Gels of different types, e.g. cross-linked alginate and shear-thinning, may be used together in a single dressing. Good results have been obtained with a shear-thinning gel nearest the skin, in use, and a cross-linked structurally reinforced gel remote from the skin.

The enzyme or enzymes may be immobilised so they can be prevented from being released into a wound, where they would have the potential to trigger undesirable allergic responses (being generally derived from non-human sources, e.g. with most commercially available glucose oxidase being derived from the fungus *Aspergillius niger* and with lactoperoxidase typically being extracted from bovine milk) and would also be susceptible to degradation by the effect of proteases present in a wound.

An enzyme may be immobilised in known manner, e.g. by being irreversibly bound to a solid support such as a particle, bead or fibre, e.g. of cellulose, silica, polymer etc., using coupling methods known to those skilled in the art. Incorporating an enzyme in a cross-linked alginate gel as discussed above, e.g. in the form of beadlets, slabs or extruded threads, also has the effect of immobilising the enzymes. Known encapsulation techniques using polyamide are also appropriate.

In embodiments using oxidoreductase enzyme and peroxidase enzyme, the two enzymes may be located in separated hydrated hydrogels, with the oxidoreductase enzyme located in a first hydrated gel and the peroxidase located in a second hydrated gel. The first and second hydrated gels can be located in different regions of the dressing as required. The dressing desirably has a layered, stratified construction, e.g. comprising an upper (outer) layer of one gel and a lower (inner) layer of another gel.

For example, the first gel (with oxidoreductase enzyme) may be located in the vicinity of the outer parts of the dressing, i.e. remote from the skin in use, where oxygen levels are highest, with the second gel (with peroxidase enzyme) being located in the vicinity of the inner parts of the dressing, i.e. adjacent the skin in use, so that the antimicrobial species (at least some of which are very short lived due to their extreme reactivity) produced thereby are close to the skin and are not expended before they reach the desired site of action. In this case the dressing thus has a layered, stratified construction, comprising an upper (outer) layer of the first gel and a lower (inner) layer of the second gel. However, experiments suggest that the relative location of the two enzymes is not critical.

Some types of dressing desirably include a layer of barrier material at the interface with the skin in use, e.g. adjacent the second gel (with peroxidase enzyme) in the arrangement above, to prevent undesirable ingress to the dressing of catalase from the skin, e.g. from wound fluid or from microbes inhabiting the area. Ingress of catalase to the dressing is undesirable as this enzyme would compete with the peroxidase for reaction with hydrogen peroxide, thus reducing efficiency. Suitable barrier material includes, e.g. a semi-permeable sheet or membrane with a relatively low molecular weight cut-off that is permeable to the antimicrobial species produced by the peroxidative peroxidase but impermeable to catalase. Suitable materials are known to those skilled in the art and include cellulose acetate film such as that used to make dialysis membranes with a molecular weight cut-off of about 15 kD.

As mentioned above, the dressing desirably includes a source of substrate for the oxidoreductase enzyme, e.g. glucose for glucose oxidase. Preferably the glucose is in the form of pure, pharmaceutical grade material. Glucose can also be supplied in the form of honey which naturally provides other benefits such as healing and antimicrobial factors. The substrate is desirably physically separated from the oxidoreductase enzyme prior to use of the dressing, to prevent premature reaction, although because oxygen is required for reaction then provided the supply of oxygen is limited only little reaction can occur. This will be discussed below. The substrate may be contained within an enclosure of a semi-permeable membrane material, e.g. material such as those used as dialysis membranes e.g. cellulose acetate (which is also often known as "visking tubing"), or within a gel slab or pad, e.g. of agarose. Such a gel slab or pad is desirably cast around a mechanical reinforcing structure, such as a sheet of cotton gauze etc., as discussed above. The substrate may conveniently be in the form of a shear-thinning gel, e.g. of a suitable gum such as xanthan gum as discussed above, preferably without a mechanical reinforcing structure, for pourable production. The substrate may alternatively be present in a hydrated gel, e.g. of hydrophilic polymer material as discussed above. The substrate, e.g. glucose is typically present in an amount up to about 25% by weight of the weight of the dressing.

It is helpful to balance the relative amounts of enzyme and substrate such that there is an excess of hydrogen peroxide which, although less potent that the products of lactoperoxidase action, can act at a greater distance than the more reactive species. It is also believed that hydrogen peroxide can stimulate the formation of new blood vessels in the recovering wound (angiogenesis, or neovascular growth), stimulate the proliferation of new tissue-forming cells and activate enzymes (proteases) responsible for helping to reshape the developing new tissue.

The substrate, e.g. glucose, may be present in various forms including dissolved within a hydrated hydrogel structure, present as a slowly dissolving solid, or encapsulated within another structure for slow release.

In the embodiment of a dressing of layered construction, as mentioned above, the source of substrate can be located (in use of the dressing) sandwiched between the upper layer of first gel containing oxidoreductase enzyme and the lower layer of second gel containing peroxidase enzyme. In this case, oxidoreductase enzyme may optionally also be included in the second gel to oxidise substrate that is liable to diffuse towards the second gel. Such oxidation is dependent on the presence of oxygen, which is in restricted supply at this location, with the oxidation reaction being proportional to the available oxygen.

In another alternative arrangement the peroxidase enzyme and substrate are both present in the second hydrated gel. In this case, the first hydrated gel (with oxidoreductase enzyme) is desirably located above and/or below the second gel in a layered arrangement.

Yet another option is to have a 4 layered structure, with an upper layer (remote from the skin) of first hydrated gel overlying a layer of substrate that overlies a further layer of first hydrated gel, in turn overlying a second hydrated gel layer at the bottom (adjacent the skin in use).

By providing an excess of substrate, so the dressing is able to function in use to generate antimicrobial species over an extended period of time, typically at least 2 days, where substrate-containing hydrated gel or gels are formulated to retard flow of substrate to the enzymes, e.g. by extensive hydrogen bonding to impede diffusion through the or from the hydrogel in which they were originally supplied.

The antimicrobial efficiency of the system can be further enhanced by the inclusion of iodide ions, which can be oxidised to elemental iodine (which is a known powerful antimicrobial agents, e.g. as discussed in WO 01/28600) by the action of hydrogen peroxide, with or without catalytic effect. Thus, the dressing desirably includes a supply of iodide ions, e.g. potassium iodide or sodium iodide. As iodine is also relatively toxic to host cells in the wound (e.g. epithelial cells, keratinocytes, white blood cells) it may not be advantageous to generate iodine continuously at a high concentration throughout the time that the formulation is in use in contact with the skin. Thus, in a preferred embodiment, the supply of iodide ions, e.g. iodide salt, is provided in a relatively quick-release form, either in the substrate gel or in an additional membrane or gauze or other suitable layer. In this way, the hydrogen peroxide produced initially, in a first phase of activity, is substantially consumed in an iodine-generating reaction, exposing the skin (e.g. wound) to a surge of iodine, the duration of which can be controlled by the amount, release-rate and position of the iodide supply. Such an iodine surge can be very useful in quickly ridding a wound of a microbial burden, and its relatively short duration allows healing by minimising damage to growing cells and their repairing activity. Once the iodide has been consumed, the system automatically reverts, in a subsequent phase of activity, to the production of hydrogen peroxide and related reactive oxygen species (ROS), which maintains sterility and kills invading bacteria near the skin, e.g. wound surface. In other embodiments, however, it may be desired for the source of iodide ions to be such as to provide, in use, a sustained flux of iodine (and/or hypoiodous acid) for release into a wound, in addition (and in proportion) to hydrogen peroxide. The supply of iodide may alternatively be located with the source of substrate for the oxidoreductase enzyme, as discussed above, e.g. in a hydrated gel. The iodide may be present in various forms, including dissolved within a hydrated gel structure, present as a slowly dissolving solid, or encapsulated within another structure for slow release. Iodide salt may be present, e.g. in an amount up to about 2% by weight. However, even in the absence of iodide, antimicrobial active intermediates are still formed, as discussed above.

In embodiments in which the enzyme or enzymes are not present in one or more hydrated gels, the enzyme or enzymes are conveniently irreversibly attached to an inert carrier or support. The support suitably comprises a gauze e.g. of woven material such as cotton or some other appropriate form of cellulose etc. The support may be activated in known manner so that it is able to react with protein (enzyme) to form stable imine bonds, so the enzyme is retained on the support. The attached enzyme may optionally be coated with a preserving agent, e.g. polyvinyl alcohol (PVA) e.g. at 5%, sucrose e.g. at 10%, gelatin e.g. at 2% and/or glycerol, to help maintain enzyme activity. The dressing is designed such that enzyme or enzymes are present in the dressing in hydrated condition.

Covalently cross-linked gels such as polyAMPS can easily be made to exclude enzyme molecules whilst being permeable to hydrogen peroxide and iodine. In gels of this nature the enzyme or enzymes can be incorporated by dosing them onto the top surface of a substrate-containing hydrogel as an aqueous solution, and allowing the liquid to soak into the gel. Although the water penetrates the gel, the enzyme molecules are retained at the top surface. If the enzyme solution contains PVA (e.g. 6% w/v), the enzyme/PVA mixture forms a thin hydrated membrane as the water is drawn into the gel. Further, the PVA matrix stabilises the enzyme with which it is associated.

It has been found that dressings in accordance with the invention act as efficient transporters of oxygen from the ambient atmosphere to a wound site, which has benefits for wound healing. In particular, the rate of oxygen transported through a dressing in accordance with the invention is greater than that of a similar dressing without oxidoreductase enzyme. The reason for this, and resulting benefits, are described below.

When a conventional dressing is applied to the surface of a wound, the supply of oxygen from the atmosphere is generally inhibited and the wound becomes relatively deprived of oxygen (hypoxic or even anoxic). Hypoxia or, worse, anoxia are frequently encountered conditions known to be very bad for wound healing, because the cells responsible for the healing (keratinocytes and epithelial cells) and the leukocytes that fight infection and control the process, all need oxygen if they are to thrive. Phagocytic leukocytes need plentiful oxygen if they are to operate their "respiratory burst" biochemistry, with which they kill bacteria. Collagen is essential for rebuilding the damaged tissues, and for creating new blood vessels (angiogenesis), which need collagen fibres on which to construct capillary walls. Collagen synthesis can only take place when hydroxylase enzymes can hydroxylate lysine and proline, to give hydroxy-lysine and hydroxy-proline, both of which are essential building blocks of collagen. Hydroxylase enzymes need a plentiful supply of oxygen for their efficient functioning. For these reasons, it is widely recognized that wounds must be well oxygenated if they are to heal efficiently, and it is frequently claimed that oxygen supply can be the rate-limiting factor in wound healing. It is believed that a failure to heal is often caused by lack of adequate oxygen. Moreover, a high oxygen tension in a wound inhibits the growth of pathogenic anaerobic bacteria, which are also responsible for malodour production.

For these reasons, certain secondary dressings, such as Tegaderm from 3M Healthcare Ltd or OpSite from Smith & Nephew (Tegaderm and OpSite are Trade Marks), are made from thin polyurethane film coated on one side with an adhesive layer. These are marketed as being relatively permeable to oxygen (and water vapour), because of their particular molecular structure and thin cross section. This is a purely passive effect, and the efficiency of oxygen permeation is inversely related to the thickness of the film.

Hydrogels are not very permeable to oxygen, because they are composed primarily of water, and oxygen is not very soluble in water. Their permeability to oxygen will also be inversely related to the thickness of the dressing. Until the advent of this invention, the only way to increase the level of oxygen in a wound was to administer oxygen to the patient, either by increasing the amount in the blood (e.g. by causing the patient to breathe oxygen-enriched air or placing the patient in a hyperbaric oxygen environment such as that available in a compression chamber), or by applying gaseous oxygen to the wound itself.

As noted above, dressings in accordance with the invention have the ability efficiently to transport oxygen from the ambient atmosphere outside the wound, into the wound bed, especially in cases where the dressing includes a layer of oxidoreductase enzyme, e.g. glucose oxidase, on the outer surface, in contact with the ambient atmosphere. Oxygen from the ambient atmosphere is converted to hydrogen peroxide (catalysed by the oxidoreductase enzyme). Hydrogen peroxide is much more soluble in water than is molecular oxygen, so hydrogen peroxide transport through the dressing (typically through one or more hydrated hydrogels) is generally much more efficient and rapid than that of molecular oxygen. Hydrogen peroxide thus diffuses rapidly through the dressing. When the hydrogen peroxide encounters catalase (which is naturally present in a wound, or which may be included as a component of the dressing), it decomposes to oxygen and water. In this way, oxygen is transported through the dressing in the form of hydrogen peroxide far more efficiently than transport of molecular oxygen. Experiments have shown that the rate of transport of oxygen can be more than doubled in dressings in accordance with the invention as compared with similar dressings without oxidoreductase enzyme. The resulting enhanced oxygen levels potentiate the healing process, as described above.

The dressing conveniently includes, or is used with, a covering or outer layer for adhering the dressing to the skin of a human or animal subject (in known manner). At least part of the covering should be of oxygen-permeable material to enable oxygen from ambient air to pass through the covering and enter into the body of the dressing in use, where it is required as a cosubstrate of the oxidoreductase catalysed reaction. The oxygen-permeable material may be in the form of a "window" set into an otherwise relatively oxygen-impermeable covering, e.g. of possibly more robust material.

Optionally the covering includes a window (or further window) in or through which can be seen indicator means e.g. an indicator sheet or similar structure that indicates (e.g. by changing colour) when the dressing chemistry is active. A further indicator may optionally be provided, which indicates (e.g. by changing colour) when the dressing chemistry has expired.

A further useful option is to provide immobilised catalase enzyme on the inner surface of the covering (e.g. secured to adhesive thereof). This will function rapidly to break down any excess hydrogen peroxide which may escape from a wound area. This feature will prevent potentially damaging build-up of hydrogen peroxide in areas of normal, undamaged skin.

The dressing may be supplied as a multi-part system, with different elements separately packaged, for assembly and use by an end user in accordance with supplied instructions. In particular, in embodiments including a source of substrate, e.g. glucose, this may be supplied packaged separately from other components, particularly the oxidoreductase enzyme, to prevent premature oxidation reaction. Alternatively, the dressing may be foldable. A typical embodiment of this sort comprises a linear arrangement of linked slabs or panels including a slab of the first hydrated gel, a slab of the second hydrated gel and a slab of substrate, with adjacent slabs linked by a respective hinge portion. Hydrophobic barrier material, e.g. a wax, is desirably impregnated into the hinge portions to prevent lateral diffusion Good results have been obtained with an embodiment comprising, in sequence, a slab of substrate, a slab of second hydrated hydrogel (containing peroxidase enzyme) and a slab of first hydrated hydrogel (containing oxidoreductase enzyme), with adjacent slabs linked by a respective foldable hinge portion. To prepare such a dressing for use the two outer slabs are folded in, to bring the slab of substrate so as to overly the slab of second gel and to bring the slab of first gel so as to overly the slab of substrate, thus forming a layered arrangement as described above. The resulting layered arrangement is placed on skin e.g. on a wound, with the slab of second gel in contact with the skin, and may be held in place e.g. by use of an adhesive covering.

One or more components of the dressing may be contained within an enclosure such as a sachet or bag of barrier material that is permeable to oxygen, water and hydrogen peroxide but that prevents undesired migration of materials. Such an enclosure has the effect, inter alia, of preventing possibly interfering substances such as catalase, iron ions etc. being taken up into the dressing from a wound site. The enclosure may also prevent undesired migration of enzyme(s) into a wound. Suitable barrier material includes e.g. a semi-permeable sheet or membrane e.g. of cellulose acetate or cellulose ester, such as one that is permeable only to molecules of molecular weight less than, say, 350 Da (possibly having a nominal molecular weight cut-off of 500 Da but with an actual limit of less than 350 Da). Suitable membranes include cellulose acetate membrane code Z368024 supplied by Sigma, Spectrum SpectraPor cellulose ester membrane code 131054 supplied by NBS Biologicals and, currently favoured particularly for an anti-acne dressing, polyurethane, e.g. Tegaderm film from 3M. (Spectrum, SpectraPor and Tegaderm are Trade Marks).

The water-absorbing components of the dressing can easily be applied to the wound or site of infection, especially when formulated into a workable or flowable form. There are many possible formulations that achieve this effect, and these can readily be determined by simple experimentation. Such formulations can be applied with particular ease and convenience from compressible tubes or syringe-like tubes (with a piston) with a nozzle of about 3 mm diameter. It can be especially helpful to supply the components in a simple assembly of two or more tubes, as required by the particular formulation in use, such that the desired mixture of gels can be expelled onto a particular site in a single action. Such multiple tube arrangements are well known and frequently used in the industry for other applications. This arrangement perfectly and conveniently satisfies the need to keep the gels apart from each other until the point of use. It has also been found that one or more of the components can be applied from a pressurised container, such that the gel is applied as a foam, spray or even an aerosol. Within the guidelines given here, the formulation that gives the particular physical properties (viscosity etc.) required for this mode of delivery can easily be determined by simple experimentation. Workable plastic gels from tubes or pressurised delivery gels can be used in combination with structured slabs to give an appropriate assembly of the basic ingredients.

Dressings of layered construction comprising shear-thinning gels can be readily produced, e.g. by an end user, by pouring or dropping the gels one on top of the other in appropriate order to produce a desired layered assembly of gels. Thus the different dressing component gels may be supplied in separate containers e.g. tubes or bottles or possibly a multi-compartment jar. The different gels may be colour-coded with appropriately coloured latex for ease of identification. The gels may be applied directly to the skin of a user. A covering or outer layer may not be required with such embodiments.

Dressings in accordance with the invention (or components thereof) are suitably supplied in sterile, sealed, water-impervious packages, e.g. laminated aluminium foil pouches.

Dressings in accordance with the invention can be manufactured in a range of different sizes and shapes for treatment of areas of skin e.g. wounds of different sizes and shapes. Appropriate amounts of enzymes, and substrates and iodide if present, for a particular dressing can be readily determined by experiment.

The invention will be further described, by way of illustration in the following Examples and with reference to the accompanying drawings, in which.

DETAILED DESCRIPTION OF EMBODIMENTS

Referring to the drawings, FIGS. 1 to 4 illustrate schematically various different embodiments of wound dressings in accordance with the invention. In all of these drawings, a cross-hatched element represents a sachet of semi-permeable membrane e.g. cellulose acetate or gel slab containing an aqueous solution of glucose and potassium iodide; an element with bold hatching lines extending from upper left to lower right represents a hydrated hydrogel slab containing glucose oxidase trapped in the gel; and an element with bold hatching lines extending from upper right to lower left represents a hydrated hydrogel slab containing lactoperoxidase trapped in the gel.

Filled circles represent beadlets of alginate gel (typically about 2 mm in diameter) containing entrapped glucose oxidase. Alternatively other gels (e.g. agarose) or polymers could be used to form the beadlets. Glucose is able to diffuse into these beadlets and hydrogen peroxide is able to diffuse out.

Empty circles represent beadlets of alginate gel (typically about 2 mm diameter) containing entrapped lactoperoxidase. Alternatively other gels (e.g. agarose) or polymers could be used to form the beadlets. Hydrogen peroxide is able to diffuse into these beadlets and reactive oxygen species are able to diffuse out.

Shaded circles represent beadlets of alginate gel (typically about 2 mm diameter) containing entrapped glucose and potassium iodide. Alternatively, other gels (e.g. agarose) or polymers could be used to form the beadlets. Glucose is able to diffuse out of these beadlets.

Figure 1:
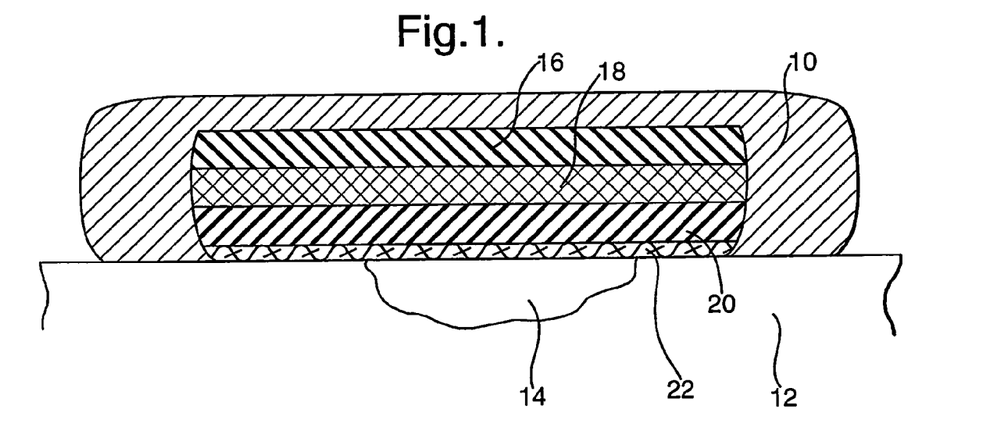
FIGS. 1 to 6 are schematic sectional illustrations of 6 different embodiments of wound dressings in accordance with the invention.

FIG. 1 illustrates one preferred embodiment of wound dressing in accordance with the invention. The dressing is of layered construction and comprises an outer layer or covering 10 in the form of an oxygen-permeable self-adhesive plaster, suitable for adhering to the skin 12 of a subject, so as to cover a wound 14. Covering 10 encloses an upper layer comprising a first moist pad 16 with immobilised glucose oxidase, an intermediate layer comprising a solution of glucose and potassium iodide in a semi-permeable sachet or gel slab 18 and a lower layer comprising a second moist pad 20 with immobilised lactoperoxidase. Below pad 20 is a sheet 22 of gauze, for contact with the wound 14. The pads and sachet may be generally as described below.

The dressing is initially supplied as a multi-part system, with the individual components separately packaged in respective sealed, sterile packages. When required for use, the dressing components are removed from the packages and applied to a wound in appropriate manner and order to produce the final dressing as shown.

Figure 2:
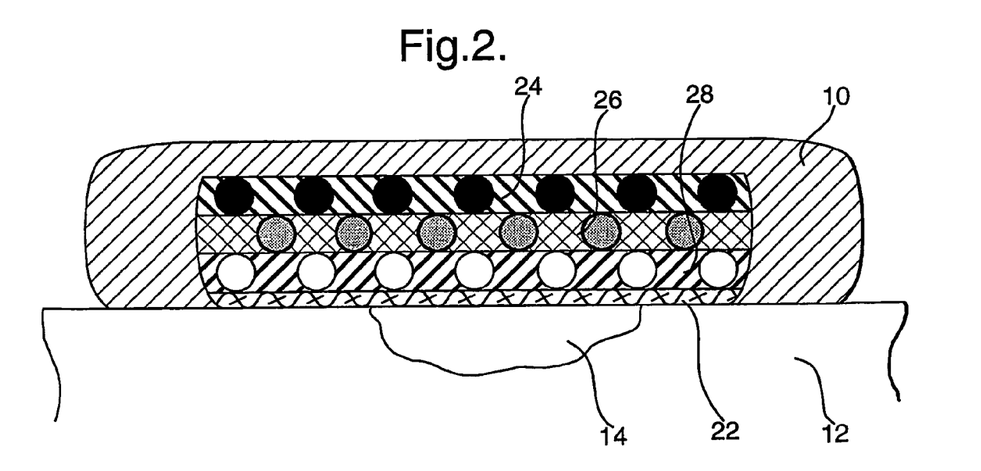

FIG. 2 illustrates another preferred embodiment of wound dressing, generally similar to FIG. 1, with similar components being identified by similar reference numerals. In this embodiment the upper layer comprises a first moist pad 24 with calcium alginate beads containing entrapped glucose oxidase. The intermediate layer comprises a pad 26 with gel beads containing glucose and potassium iodide. The lower layer comprises a second moist pad 28 with calcium alginate beads containing entrapped lactoperoxidase.

Figure 3:
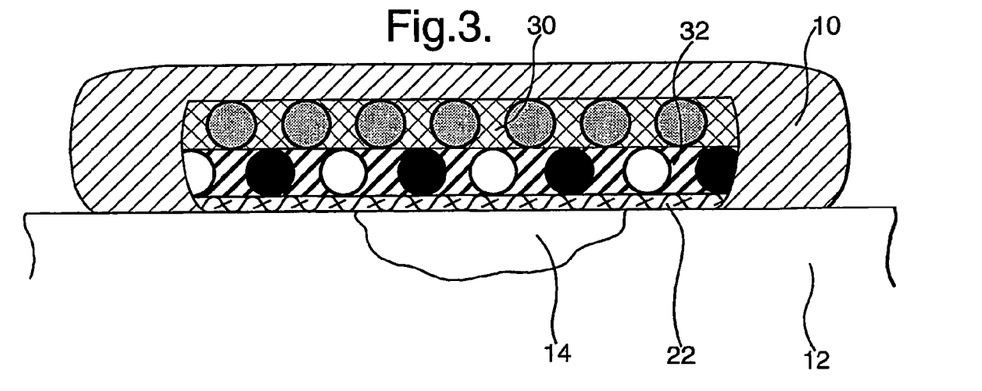

FIG. 3 illustrates a further generally similar embodiment, but comprising an upper layer in the form of a pad 30 with gel beads containing glucose and potassium iodide, and a lower layer comprising a moist pad (or gel slab) 32 with calcium alginate beads containing entrapped glucose oxidase and calcium alginate beads containing entrapped lactoperoxidase.

Figure 4:
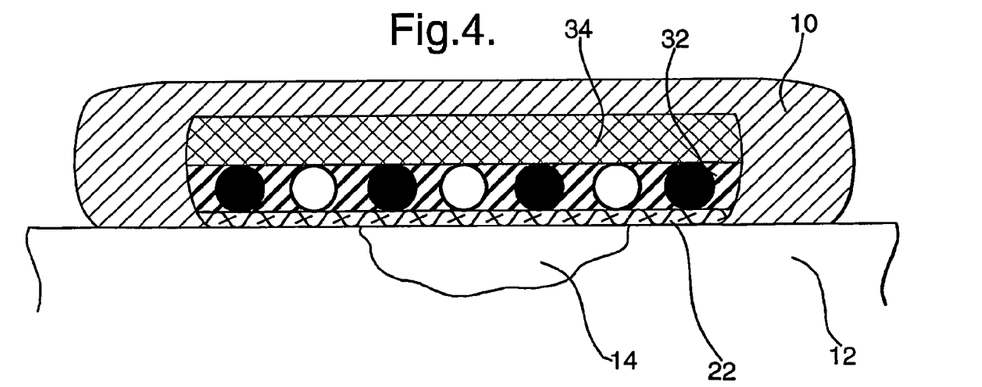

FIG. 4 is a variant of FIG. 3 in which the upper layer comprises a semi-permeable sachet or gel slab 34 containing glucose and potassium iodide.

EXAMPLES

Construction of Glucose Oxidase and Lactoperoxidase Beadlets.

The enzyme, either lactoperoxidase (LPO) (from Sigma, cat no L2005) or glucose oxidase (GOX) (from Boehringer Mannheim, Cat No. 105147) is dissolved in pure water at the rate of 1 microgram per ml LPO) or 10 micrograms per ml (GOX). A solution of alginic acid (Manucol DM (Manucol DM is a Trade Mark) from C P Kelco) (1 gram per 100 ml of water) is prepared at elevated temperature and cooled. Enzyme solution is mixed with the cooled alginic acid at the appropriate rate. The resulting alginic acid/enzyme solution is then pumped through a peristaltic pump into a tube which leads to an exit nozzle conveniently formed by a standard laboratory glass pasteur pipette, placed over a setting bath of calcium chloride solution (10% w/v). The flow of the pump and height of the exit nozzle are adjusted so that the outflowing stream of alginic acid/enzyme solution forms into discrete droplets as it enters the calcium chloride solution. Each droplet rapidly starts to solidify as the calcium begins to cross-link the alginic acid molecules and, 10 minutes after the delivery of the last droplet, the setting process is complete. All the newly formed beadlets are removed from the calcium chloride solution by pouring the whole through a sieve of suitable mesh size. Residual calcium chloride is removed by rinsing with pure water. The beadlets are stored in water or in water-tight containers, or in a physiological buffer solution such as phosphate buffered saline. Alternatively, they can be placed in glycerol or glycerol in water solutions to decrease the entrained water content. Whatever storage conditions are used, they must not be allowed to dry out or harden in the absence of water or glycerol.

Construction of Glucose Beadlets.

The method described above is followed, except that no enzymes are added and glucose is included at the rate of 12.5 g per 100 ml in both the pure water and the calcium chloride setting bath. The gel beadlets are washed with calcium-free glucose solution, allowing removal of excess calcium without depleting the glucose.

Preparation of an Enzyme Beadlet-Containing Pad.

Appropriately sized cotton lint is placed on a suitable surface through which water can flow (e.g. a flat plastic mesh). A suspension of enzyme-beadlets is poured onto the cotton lint, in such a way that the beadlets become entrapped in the raised nap of the fabric, as the suspending water flows away. A second piece of lint is then placed over the first, so as to sandwich the enzyme beadlets between the two fabric layers. Adhesive or stitching or stapling may be used to secure the top layer to the bottom layer. Excess fluid is drained away, but the pad is not allowed to dry out.

The number of beadlets contained per pad should be determined on the basis that each oxidase pad should carry about 100 mg of GOX, and each peroxidase pad should carry about 10 mg of LPO.

Preparation of a Pad Containing Glucose Beadlets and Iodide

The method described above is used with glucose-containing beadlets to prepare a pad containing entrapped glucose, except that an extra step is included at the end of the process, in which the pad is soaked in a solution of potassium iodide (10 mM).

Preparation of a Glucose/Iodide Containing Sachet.

Glucose is dissolved in a 5 mM aqueous solution of potassium iodide at the rate of 12.5 g per 100 ml. This solution is then placed in a dialysis bag (previously placed in boiling water for 10 mins and thoroughly rinsed) with an accessible area of about 40×20 mm, and sealed.

Demonstration of the Oxidative Activity of an Assembled Composite Dressing.

A 1% aqueous solution of agarose is prepared, with potassium iodide added at a concentration of 10 mM and soluble starch at concentration of 1% w/v. The solution is melted and dispensed into a petri dish to form a continuous layer about 5 mm thick, and allowed to set. Once set a peroxidase pad as described above is laid on the surface, followed by a glucose pad or sachet as described above laid on top of that, and finally a glucose oxidase pad as described above is laid on top of them both to form a three-layered stack. The development of a blue colour within the starch agar indicates the oxidative activity of the composite dressing.

Use of the Assembled Composite Dressing as a Wound Treatment.

The pads or sachets for this purpose prepared as described above are sealed in appropriate pouches and subjected to gamma irradiation to ensure microbiological sterility, using techniques known and routinely used in the industry.

Firstly the wound is covered by a thin sheet of sterile gauze. Next the three layers of sterile pads are added as a thin stack, with the peroxidase pad first followed by the glucose pad or sachet next and the glucose oxidase pad last. The pads are cut to a size that just covers the open wound. Finally, the composite dressing is preferably held in place by adhesive film, such as normal "sticking plaster" or "Micropore" surgical tape.

Other Embodiments

The enzymes can be immobilised on various types of particle or fibre, using coupling methods known by those skilled in the art. The particles can be made of cellulose, silica or various harmless polymers. Alginate can be used in forms other than beadlets, such as slabs or extruded threads, still using calcium as a setting agent. Microcapsules, such as those made by known techniques with polyamide, can be used to encapsulate each of the components.

Further dressing components were prepared as follows.

Preparation of an Enzyme-Containing Pad

Loose woven cotton gauze is cut into a number of pieces approximately 100 mm by 100 mm and each piece is laid into a respective suitable flat bottomed container. 1% w/v alginic acid (also termed "alginate"; e.g. Manucol DM (Manucol DM is a Trade Mark), from CP Kelco) is prepared by dissolving the gel into an appropriate, heated aqueous solution. After cooling, enzyme is added to the alginate, to give a final concentration of 5 µg/ml glucose oxidase (GOX, from Boehringer Mannheim, cat. no.: 105147) or 10 µg/ml lactoperoxidase (LPO, from Sigma, cat. no.: L2005). 10 mls of each enzyme-alginate solution is prepared, and poured evenly onto the individual cotton gauze pads. The gel is set by the addition of excess 10% w/v calcium chloride ($CaCl_2$) and allowed to stand for 10 minutes. The pads are then washed twice for 5 minutes each, in excess distilled/deionised water to remove the $CaCl_2$. The pads can then be stored in a humid environment to prevent drying out.

Preparation of Glucose-Containing Pad

Loose woven cotton gauze is cut to approximately 100 mm by 100 mm and is laid into a suitable flat bottomed container. 1% w/v agarose and 40% w/v glucose is dissolved into an appropriate aqueous solution and poured onto the gauze while still molten. The gel is allowed to set by cooling. The gel pad can then be stored in a humid environment to prevent drying out. To produce a pad containing glucose and potassium iodide, a similar procedure is followed, but after the glucose and agarose have been dissolved, potassium iodide (KI) is added to a final concentration of 10 mM. The solution can then be poured, allowed to set and stored as above.

Demonstration of the Anti-Microbial Properties of an Assembled Composite Dressing Example 1

Using standard practices, a 1.5% agarose microbial growth plate is prepared, but with the glucose replaced by fructose as the sole carbon source. The plates are typically in the region of 5 mm thick. *Pseudomonas aeruginosa* was spread over the surface of the plate in an even "lawn". A pad containing LPO-alginate prepared as described immediately above) of approximately 20 $mm^2$ was placed onto the surface of the plate. Placed directly onto this pad is a 20 $mm^2$ pad containing glucose-agar (prepared as described immediately above) (with or without KI). Finally, a 20 $mm^2$ pad containing GOX-alginate (prepared as described immediately above) was layered onto the glucose-agar pad. A clearance zone around the pad stack can be clearly seen after 24 hours, showing the production and diffusion of active anti-microbial species, preventing the growth of the applied bacteria. Removal of any one of the 3 pads (control experiments) results in no clearance zone around the pad stack, showing that both enzymes and glucose all need to be present for the cascade to progress effectively.

Example 2

Alternatively, to show the production of reactive oxidative species via the stacked enzyme system, a 1% w/v agar plate is cast, that includes 1% soluble starch (e.g. ARCOS cat. no.: 177132500) and 10 mM KI. The plate is allowed to set by cooling. The LPO-alginate pad, followed by the glucose-agar pad and finally the GOX-alginate pad can then be stacked as described above in Example 1. The production of the reactive oxidative species can be then visualised by the intense blue coloured chromogen produced by the well documented interaction of elemental iodine (the oxidative species oxidise the iodide to iodine) and starch. This coloration can be clearly seen after 5 minutes, with the intensity and spread building over time. After 30 minutes, the colour intensity has built to become a deep blue, indicating continued product formation. This shows that both reactive oxidative species and iodine are produced, both of which aid in the anti-microbial activity of the composite dressing.

Example 3

A variation on Example 2 is to include a low level of GOX (0.25 µg/ml) in the LPO-alginate pad, to promote an initial production of reactive oxidative species. This utilises oxygen available in the gel, and is initiated by the glucose that is diffusing into the LPO-alginate pad. This reaction is limited, due to the availability of oxygen and will cease when the oxygen is depleted. To show the production of reactive oxidative species via the stacked enzyme system, a 1% w/v agar plate is cast, that includes 1% soluble starch (e.g. ARCOS cat. no.: 177132500) and 10 mM KI. The plate is allowed to set by cooling. The combined LPO and GOX-alginate pad, followed by the glucose-agar pad and finally the GOX-alginate pad can the be stacked as described above. The accelerated production of the reactive oxidative species can be then visualised by the intense blue coloured chromogen produced by the well documented interaction of elemental iodine (the oxidative species oxidize the iodide to iodine) and starch. This coloration can be clearly seen after as little as 1 minute, with the intensity and spread building over time. The coloration will slow down noticeably after 15 minutes if the top GOX-alginate pad is not used. If the GOX-alginate pad is used as described above, the coloration will continue strongly, as seen in Example 2 above. After 30 minutes, the colour intensity has built to become a deep blue, indicating continued product formation. This shows that both reactive oxidative species and iodine are produced, both of which aid in the anti-microbial activity of the composite dressing.

Further work was carried out using relatively high concentration xanthan gum gels.

Preparation of Enzyme-Containing Xanthan Gum/Alginate Gels

A series of solutions of xanthan gum (Keltrol) were prepared at different concentrations (5%, 10% and 20% by weight) by dissolving appropriate amounts of Keltrol into distilled/de-ionised water at room temperature (about 20° C.). A series of solutions of alginic acid (Manucol DM (Manucol DM is a Trade Mark) from CP Kelco) at different concentrations (2% and 4% by weight) were also prepared by dissolving appropriate amounts of Manucol DM into distilled/de-ionised water at appropriate elevated temperature. The resulting alginic acid solutions were cooled.

A series of xanthan gum/alginate gels including the two materials in different proportions were prepared by mixing the solutions in appropriate quantities until a homogeneous mixture was obtained. For example, gels were prepared having a weight ratio of xanthan gum to alginate of 5:1 (e.g. by mixing equal amounts of 5% and 1% solutions or 10% and 2% solutions), 5:2, 10:1 etc. as required.

Enzyme-containing gels were prepared by the addition of the appropriate quantity of glucose oxidase (GOX) or lactoperoxidase (LPO) enzymes to the gel samples. Enzyme solution may be added either to a xanthan gum or alginate solution prior to mixing, or to a xanthan gum/alginate gel after mixing. Experiments were carried out using LPO from Sigma, (catalogue number L2005) dissolved in pure water at the rate of 1 microgram per milliliter and GOX from Boehringer Mannheim (catalogue number 105147) dissolved in pure water at the rate of 10 micrograms per milliliter.

Construction of Cross-Linked Xanthan Gum/Alginate Gel Pads Supported by Cotton Gauze A 10% xanthan gum 2% alginic acid gel mixture was prepared by mixing equal volumes of stock 20% xanthan gum solution and 4% alginic acid solution, prepared as described above. LPO and GOX were added to separate samples of this gel mixture to produce an LPO-containing gel and a GOX-containing gel. Enzyme levels can be varied according to the required level of activity. In this case enzyme levels used were 100 µg/ml for LPO and 50 µg/ml for GOX.

Approximately 5 ml of the LPO-containing gel was smoothed onto a strip of cotton gauze approximately 40 mm×50 mm. A second layer of gauze of similar size was placed on top of the LPO gel with light pressure to ensure an even distribution of the gel. Approximately 5 ml of the GOX-containing gel was then dispensed onto the upper face of the second layer of cotton gauze, with a third layer of gauze of similar size applied on top of the GOX-containing gel, again with light pressure to ensure an even distribution of the GOX-containing gel. This produced a pad or slab of sandwich construction comprising three sheets of cotton gauze separated, respectively, by a layer of LPO-containing gel and a layer of GOX-containing gel.

The resulting pads were placed in a bath of calcium chloride solution (10% w/v) for 10 minutes. The pads were removed from the bath and then washed to remove residual calcium chloride by two 10 minute washes in distilled/de-ionised water. Excess water was removed by drying the pads for several minutes in absorbent tissue.

Demonstration of the Activity of the Cross-Linked Xanthan Gum/Alginate Gel Pad

Example 4

The starch/iodine complex reaction was used to visualise the enzymatic production of reactive oxidative species (ROS) from within the cross-linked xanthan gum/alginate gel pad, prepared as described previously. In the presence of ROS, iodide is oxidised to produce elemental iodine, which complexes with starch to produce an intense blue chromogen.

Experiments were carried out using a 1% w/v agar plate that includes 1% soluble starch (ARCOS catalogue number 177132500) and 10 mM potassium iodide. A slice of the cross-linked xanthan gum/alginate pad as described above (approximately 20 mm×10 mm×4 mm) was placed on the starch/iodide plate, with the GOX layer uppermost. On top of this was placed a pad of gel comprising 40% glucose in 1% agar to initiate the reaction. After about 30 minutes the lower pad had turned yellow, clearly indicating the production of elemental iodine (iodide being present due to diffusion from the plate into the gel). After about 1 hour, blue staining was visible beneath the pad, indicating the presence of ROS within the starch/iodide plate. 24 hours after initiation, a large area of the plate had turned blue, indicating continued production of ROS.

Example 5

Two similar experiments were carried out using an arrangement generally as described above in Example 4 but with the glucose pad below the cross-linked xanthan gum/alginate pad. Two experiments were carried out, with the xanthan gum/alginate gel pads in different orientations, in one case with the GOX layer uppermost and with the other with the LPO layer uppermost.

With the pad positioned with the GOX layer lowermost, next to the glucose pad, after approximately 1 hour blue staining could be seen under the pad. With the other experiment, with the LPO layer lowermost, next to the glucose pad, after about 2 hours blue staining could be seen under the pad. This shows that even with an arrangement using a pad with enzymes in non-optimal sequence, ROS can still be produced in sufficient quantity to produce an oxidative effect in the indicator plate.

In both experiments, yellow coloration was seen in both gels, in the LPO layers, showing the presence of iodine production. After 24 hours, in both cases much of the starch/iodide plate had turned blue, again showing the production of ROS.

Demonstration of the Moisture Absorbency of a Xanthan Gum Gel

A 10% by weight preparation of Keltrol in water was prepared as described above. 1.06 g of the 10% gel was added to 10.22 g of distilled/de-ionised water, maintained at 21° C. and sealed to minimise evaporation effects. The water was decanted off and measured by weight to assess the degree of absorbency.

After 15 minutes, 8.34 g of water remained; after 45 minutes, 7.56 g remained; after 2 hours 6.51 g remained; after 18 hours, 2.1 g remained.

This experiment shows that the 10% Keltrol gel is able to absorb at least 8 times its weight in water.

Demonstration of the Moisture Absorbency of a Cross-Linked Xanthan Gum/Alginate Gel Mixture A mixture of 5% by weight Keltrol and 1% by weight alginic acid was prepared as described above. Two layers of gel were cast between two layers of cotton gauze to produce a pad that was cross-linked using a 10% calcium chloride solution and washed twice for 10 minutes in water, as described above. The pad was blotted dry using absorbent tissue paper.

A piece of the pad 10 mm×10 mm×3 mm was weighed to establish the initial weight (0.28 g). 1 ml of water was added to the pad. The pad was removed and weighed after various times to assess the increase in weight (due to absorption of water). After one 1 hour the weight of the pad was 0.37 g; after 2 hours 0.44 g; after 3 hours 0.49 g and after 6 hours 0.5 g.

This experiment shows that the cross-linked xanthan gum/alginate gel is still able to absorb water. Compared with the Example above using 10% Keltrol, use of a lower percentage of Keltrol and cross-linked alginate results in less water absorbency.

Cross-linked xanthan gum/alginate gels prepared as described above were used in the production of a wound dressing in accordance with the invention, as shown schematically in FIG. 1. Such gels were used together with a glucose/iodide containing sachet prepared as described above. In particular, glucose was dissolved in a 5 mM aqueous solution of potassium iodide at the rate of 12.5 g per 100 ml. The solution was placed in a dialysis bag (previously placed in boiling water for 10 minutes and thoroughly rinsed) with an accessible area of about 40×20 mM, and sealed.

The components were assembled to form a dressing of the construction shown in FIG. 1. The dressing is of layered construction and comprises an outer layer or covering 10 in the form of an oxygen-permeable self-adhesive plaster, suitable for adhering to the skin 12 of a subjects so as to cover a wound. Covering 10 encloses an upper layer comprising a pad of glucose oxidase-containing cross-linked xanthan gum/alginate gel, prepared as described above; an intermediate layer comprising a solution of glucose and potassium iodide in a semi-permeable sachet 18, prepared as described above; and a lower layer comprising a slab of lactoperoxidase-containing cross-linked xanthan gum/alginate gel prepared as described above. Below pad 20 is a sheet 22 of gauze, for contact with the wound 14.

The dressing is initially supplied as a multi-part system, with the individual components separately packaged in respective sealed, sterile packages. When required for use the dressing components are removed from the packages and applied to a wound in appropriate manner in order to produce the final dressing as shown.

Figure 5:
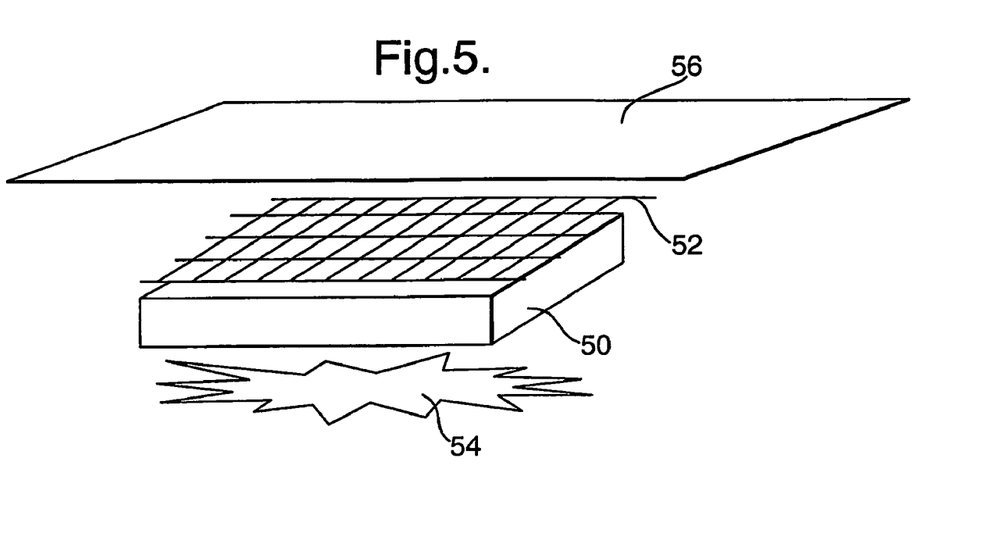

FIG. 5 illustrates schematically a further embodiment of dressing in accordance with the invention, wherein the dressing comprises a lower layer 50 which is a hydrogel slab comprising glucose and iodide salts; an upper layer 52 remote from the skin in use, comprising glucose oxidase; and an overlayer 56. This form of dressing is currently favoured. The dressing has major dimensions of 100 mm×100 mm, in the form of a square.

The illustrated dressing comprises a soft, hydrated hydrogel slab 50 composed of polyAMPS (as described in WO 01/96422 supplied by First Water Ltd). The hydrogel contains up to 23% glucose (which acts as a substrate for oxidoreductase enzyme) and iodide salts e.g. 1.6% w/v potassium iodide (which are a precursor to iodine). The hydrogel may also contain up to 20% w/v glycerol (which acts as a humectant and moisturiser). The hydrogel slab 50 forms the lower layer of the dressing.

The dressing also comprises an upper layer constituted by a cellulose woven gauze 52 to which are irreversibly (covalently) bound glucose oxidase and lactoperoxidase. The gauze 52 is prepared as follows.

The gauze is cut to a suitable size and shape (a square 100 mm×100 mm), and is washed in water to remove any solutes or particulates. Excess fluid is removed. The gauze is then soaked in a solution of 10 mM sodium meta-periodate for 60 minutes at 25° C. After this oxidation step, where reactive aldehyde groups are formed, the gauze is extensively washed in water to remove the periodate. After the wash step, the gauze is soaked in a solution of glucose oxidase (Biocatalysts—Code G638P), at 100 μg powder per ml 50 mM sodium hydrogen carbonate at pH 9.0. This is equivalent to 7000 U/ml. Lactoperoxidase (DMV International) is also incorporated at 100 μl powder per ml 50 mM sodium hydrogen carbonate at pH 9.0. These doses can be reduced, since they represent an excessive amount of activity. The gauze is left to react with the enzyme solution for 4 hours at about 20° C., after which the gauze is removed and washed extensively between low ionic strength solution (deionised water) and high ionic strength buffer (50 mM $NaH_2CO_3$ pH 9.0+1M NaCl) to remove loosely bound enzyme. The gauze is then coated in a preservative, for example 5% PVA, 10% sucrose or 2% gelatin and dried either at room temperature (approximately 21° C.) or, preferably, at 40° C.

The lower and upper layers are assembled with each other in a nitrogen atmosphere (to prevent premature reaction), and are packaged together by being sealed in an oxygen-impermeable pouch or enclosure, e.g. made of laminated aluminium foil pouches as supplied by Sigma (code Z183407). The interaction of the glucose in the gel with the immobilised glucose oxidase is limited by the rate at which the glucose can diffuse into the immobilised-enzyme layer. This delay is sufficient to allow the two layers to be assembled together in the presence of oxygen, and then placed in an oxygen-free package, before any substantial reaction can take place. Once oxygen is excluded from the assembled product, the reaction is arrested anyway, and it can only resume when the oxygen supply is renewed (e.g. when the product is removed from the packaging for use on a wound). This oxygen deprivation within the packaging prevents the glucose from being used up in premature peroxide production. The enzymes, while initially in dry form on the gauze on assembly, become hydrated with water from the hydrogel slab 52 and are maintained in hydrated condition by water from the hydrogel slab 52 while sealed in the pouch or enclosure prior to use.

In use, the dressing is removed from the pouch or enclosure and placed on the skin of a patient over a wound site, shown schematically at 54, with the lower hydrogel layer 50 in contact with the skin. An oxygen-permeable and moisture-permeable covering or overlayer 56 (which may or may not form part of the dressing) is located over the upper layer 52 and is adhered to the skin surrounding the wound site by means of suitable adhesive provided on the lower face of overlayer 56. In this way the dressing is retained in position on the skin, covering the wound site.

The glucose oxidase in the upper layer (which is in hydrated condition) catalyses reaction of the glucose in the lower layer with oxygen that passes through the overlayer 56 from the surroundings, producing hydrogen peroxide as discussed above. The hydrogen peroxide itself has beneficial antimicrobial effects, as discussed above. The hydrogen peroxide also undergoes a further reaction catalysed by the lactoperoxidase to produce a variety of species with antimicrobial properties, as discussed above. In addition, the iodide salts in the lower layer react to produce elemental iodine and possibly also hypoiodous acid, further powerful antimicrobial agents, as discussed above. The dressing thus has a number of very effective mechanisms for in-situ production of antimicrobial agents that can be very effective in promoting wound healing.

Further, the hydrogel of the lower layer is highly fluid absorbent, allowing the take-up of high volumes of exudate from the wound. Fluid exuded from the wound, including potentially harmful bacteria etc, can thus be absorbed into the dressing and killed by the antimicrobial species generated therein. The dressing can thus be self-sterilising. The hydrogel is also able to donate fluid, should the wound require it, thus allowing the wound site to be kept moist at all times aiding the healing process.

In a modification of the FIG. 5 embodiment described above, no lactoperoxidase is present. In this case, although the hydrogen peroxide produced by the reaction catalysed by the glucose oxidase does not undergo lactoperoxidase-catalysed reaction, nevertheless useful amounts of the hydrogen peroxide spontaneously undergo non-catalysed reaction with iodide ions to generate molecular iodine and valuable antimicrobial effects are nevertheless still obtained.

Figure 6:
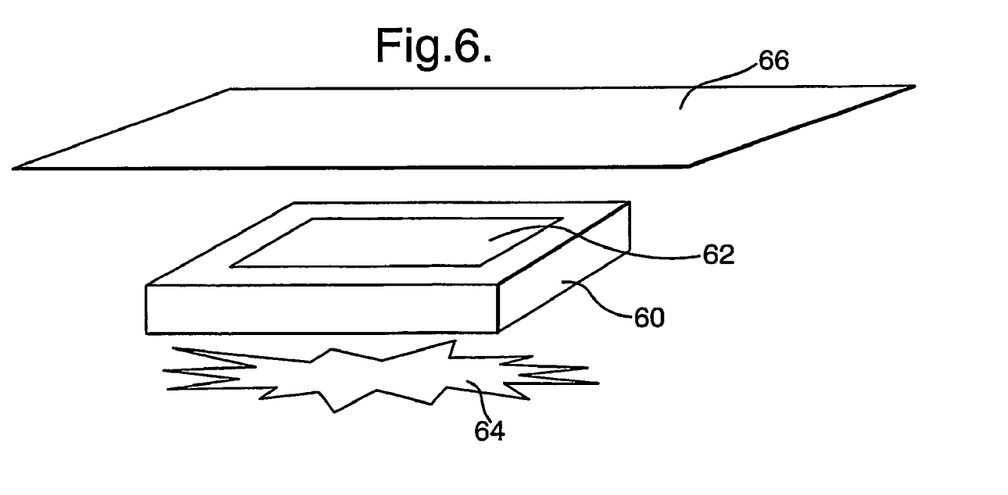

FIG. 6 illustrates schematically yet a further embodiment of dressing in accordance with the invention, wherein the dressing comprises a hydrogel lower layer 60 comprising glucose, an enzyme-containing PVA film 62, and an overlayer 66. The dressing has major dimensions of 100 mm×100 mm, in the form of a square.

The illustrated anti-bacterial and anti-fungal wound dressing comprises a glucose-containing hydrogel slab 60 as the lower layer of the dressing. Cast onto the upper surface of slab 60 is a film 62 of PVA (polyvinyl alcohol) that incorporates glucose oxidase.

The hydrogel lower layer 60 was formulated to include the following reagents by weight: 20% sodium AMPS (2-acrylamido-2-methylpropanesulfonic acid, sodium salt (Lubrizol, code 2405)), 20% glucose (Fisher, analytical grade), 10% glycerol (Fisher, analytical grade), 50% deionised water, 0.1% poly ethylene glycol 400 diacrylate (UCB Chemicals) and 0.01% photoinitiator (1-hydroxycyclohexyl phenyl ketone (Aldrich)). The mixture was dispensed into casting trays, to a depth of 2-3 mm. The hydrogel was then set, by irradiation under a UV lamp, for up to 60 seconds and a power rating of approx. 100 $mW/cm^2$. The hydrogel was then allowed to cool to 30° C. or below.

The enzyme-containing PVA film 62 was prepared by dissolving high molecular weight PVA (124,000-186,000 mw, Aldrich) in water by heating the mixture. The PVA was incorporated to a final concentration of 6% w/v. Once dissolved, the solution was allowed to cool to 30° C. or below, before enzyme (glucose oxidase (GOX, Biocatalysts G638P)) was added, to a concentration of 100 μg/μl (weight freeze dried powder per volume). 50-100 μl of the PVA/GOX mixture was then added to a 20 $mm^2$ surface of the cooled hydrogel, and allowed to set. A thin film was formed after approximately 30mins. To prevent enzyme activation, the addition of the PVA/GOX solution to the glucose hydrogel may be carried out in an oxygen-free atmosphere (e.g. under nitrogen). When film 62 contacts the hydrogel 60, most of the water from the film is drawn into the hydrogel, leaving the PVA as a moist membrane containing the enzyme in hydrated condition. Sufficient water remains in the film for the PVA to be hydrated and to remain flexible.

The resulting dressing is packaged in an oxygen-impermeable pouch or enclosure, e.g. made of laminated aluminium foil pouches as supplied by Sigma (code Z183407). The interaction of the glucose in the gel with the immobilised glucose oxidase is limited by the rate at which the glucose can diffuse into the immobilised-enzyme layer. This delay is sufficient to allow the two layers to be assembled together in the presence of oxygen, and then placed in an oxygen-free package, before any substantial reaction can take place. Once oxygen is excluded from the assembled product, the reaction is arrested anyway, and it can only resume when the oxygen supply is renewed (e.g. when the product is removed from the packaging for use on a wound). This oxygen deprivation within the packaging prevents the glucose from being used up in premature peroxide production. The enzyme is maintained in hydrated condition while sealed in the pouch or enclosure prior to use.

In use, the dressing is removed from the pouch or enclosure and placed on the skin of a patient over a wound site, shown schematically at 64, with the lower hydrogel layer 60 in contact with the skin. An oxygen-permeable and moisture-permeable covering or overlayer 66 (which may or may not form part of the dressing) is located over the film 62 and is adhered to the skin surrounding the wound site by means of suitable adhesive provided on the lower face of overlayer 66. In this way the dressing is retained in position on the skin, covering the wound site.

The glucose oxidase in the film 62 (which is in hydrated condition) catalyses reaction of the glucose in the lower layer with oxygen that passes through the overlayer 66 from the surroundings, producing hydrogen peroxide as discussed above. The hydrogen peroxide has beneficial antimicrobial effects, as discussed above, and the oxygen released when it is decomposed by endogenous catalase aids the healing process by supporting cellular metabolism, potentiating amino acid hydroxylation and inhibiting the growth of anaerobic bacteria.

To demonstrate the generation of oxidative species, an indicator plate consisting of 1% starch (Aldrich), 100 mM potassium iodide (Fisher) and 1% agar (Sigma) was used. The dressing comprising hydrogel 60 with PVA/GOX film 62 was placed onto the indicator plate, in air, with the GOX thus being activated through the available oxygen. Hydrogen peroxide is produced in sufficient quantity to be able to diffuse through the hydrogel and reach the indicator plate below. The oxidative power of the hydrogen peroxide then oxidises iodide to iodine, which complexes with the starch to form an intense dark blue complex. By removing the activated hydrogel dressing and placing it onto new indicator plates at 24 hour intervals, sustained hydrogen peroxide release can be demonstrated over a period of at least 5 days.

In addition, to demonstrate further the stability of the GOX enzyme in the PVA film, the film was removed from a hydrogel after 4 days use, and placed onto fresh 20 mm$^2$ glucose hydrogel and placed onto an indicator plate. After 24 hours, the intense blue starch/iodide complex was clearly visible, indicating enzyme activity was still present in the PVA film.

To demonstrate the localised GOX activity in a glucose-free hydrogel, a PVA/GOX film was produced as described above. The hydrogel was placed onto a bed of PBS (phosphate buffered saline) saturated cotton gauze, and allowed to swell slowly over 24 hours. The hydrogel was then sliced into two, through the horizontal plane, and bathed in a solution of 1% starch+100 mM potassium iodide+1% w/v glucose+5 mM EDTA+50 µg/ml lactoperoxidase. Very quickly, the presence of GOX can be localised, by the detection of hydrogen peroxide. The GOX activity is clearly localised to the PVA film and the contact surface of the hydrogel where the PVA film was cast. Beneath this, there was no colour generation, thus showing that GOX is not mobile in the AMPS hydrogel, even in a swollen state.

The hydrogel slab 60 is highly fluid-absorbent, and so has the properties and benefits describes above in connection with the FIG. 5 embodiment.

The invention claimed is:

1. A skin dressing comprising a layered construction, said layered construction including one or more oxidoreductase enzymes in hydrated condition and present in sufficient amount to catalyze, in the presence of appropriate substrate, the conversion of atmospheric oxygen to hydrogen peroxide for transmittal through the dressing to the skin, wherein at least the enzyme-containing layer of the dressing is sealed in packaging and maintained in hydrated and sterile condition in said packaging up to use, wherein said layered construction comprises an upper layer and a lower layer, said upper layer being remote from the skin in use and including the oxidoreductase enzyme, and said lower layer being below the upper layer in use such that hydrogen peroxide which is formed and transported through the dressing is discharged at the skin for conversion to oxygen, said lower layer comprising a hydrogel including said source of substrate for the oxidoreductase enzyme, said oxidoreductase enzyme being included only in said upper layer and remaining in the upper layer in use.

2. The skin dressing according to claim 1, wherein the one or more oxidoreductase enzymes comprise glucose oxidase and the substrate is β-D glucose.

3. The skin dressing according to claim 1, wherein at least one of the layers is in the form of a hydrated hydrogel.

4. The skin dressing according to claim 3, wherein the hydrated hydrogel comprises a hydrophilic polymer material.

5. The skin dressing according to claim 3, wherein the oxidoreductase enzyme or enzymes are present in one or more hydrated hydrogels.

6. The skin dressing according to claim 1, wherein the one or more enzymes are located on an inert support.

7. The skin dressing according to claim 6 wherein the inert support comprises a cotton or cellulose woven gauze to which the one or more enzymes are irreversibly attached.

8. The skin dressing according to claim 1, including a layer of a barrier material at the interface with the skin in use.

9. The skin dressing according to claim 1 including a covering or outer layer for adhering the dressing to the skin of a human or animal subject.

10. The skin dressing according to claim 9, wherein the covering or outer layer includes a window in or through which can be seen indicator means that indicates when the dressing chemistry is active.

11. The skin dressing according to claim 9, wherein immobilised catalase enzyme is provided on the inner surface of the covering or outer layer.

12. The skin dressing according to claim 1, in the form of a multi-part system, with different layers separately packaged for subsequent combination when used.

13. The skin dressing according to claim 12, said dressing being in the form of a multi-part system, with different elements comprising said layers separately packaged, and wherein the oxidoreductase enzyme and the substrate for the oxidoreductase enzyme are in separate packages.

14. The skin dressing according to claim 1, wherein the lower layer further includes a supply of iodide ions.

15. The skin dressing according to claim 1 wherein said layers are free from peroxidase enzyme and the oxidoreductase enzyme is included only in the upper layer.

16. The skin dressing of claim 1 wherein the upper layer is in the form of a gauze or film and the lower layer comprises a hydrogel slab.

17. A layered dressing for treatment of skin wounds comprising
an upper layer intended to be remote from the skin in use, said upper layer being permeable to atmospheric oxygen and including at least one oxidoreductase enzyme; and
a separate lower layer comprising a hydrogel including a source of substrate for said oxidoreductase enzyme, said lower layer being free from any oxidoreductase enzyme and being positioned below the upper layer in use,
wherein the oxidoreductase enzyme in said upper layer is in a hydrated condition and is present in an amount sufficient, in the presence of the substrate, to catalyze conversion of atmospheric oxygen entering said upper layer into hydrogen peroxide wherein construction of the upper and lower layers allows for transportation of the thus formed hydrogen peroxide through the lower layer to the skin for conversion to oxygen; and wherein at least the upper layer of the dressing before use is sealed in packaging in the hydrated condition.

* * * * *